United States Patent
Wenstrand et al.

(10) Patent No.: US 8,999,003 B2
(45) Date of Patent: Apr. 7, 2015

(54) CONTROL SYSTEM FOR PROSTHETIC LIMB

(75) Inventors: Douglas S. Wenstrand, Elkridge, MD (US); Stuart D. Harshbarger, Woodbine, MD (US)

(73) Assignee: The Johns Hopkins University, Baltimore, MD (US)

( * ) Notice: Subject to any disclaimer, the term of this patent is extended or adjusted under 35 U.S.C. 154(b) by 337 days.

(21) Appl. No.: 13/601,262

(22) Filed: Aug. 31, 2012

(65) Prior Publication Data

US 2014/0067083 A1    Mar. 6, 2014

(51) Int. Cl.
| | | |
|---|---|---|
| A61F 2/70 | (2006.01) |
| A61F 2/54 | (2006.01) |
| A61F 2/68 | (2006.01) |
| A61F 2/58 | (2006.01) |
| A61F 2/50 | (2006.01) |
| A61F 2/72 | (2006.01) |
| A61F 2/76 | (2006.01) |

(52) U.S. Cl.
CPC ........... *A61F 2/68* (2013.01); *A61F 2002/5058* (2013.01); *A61F 2002/5083* (2013.01); *A61F 2002/689* (2013.01); *A61F 2002/704* (2013.01); *A61F 2/72* (2013.01); *A61F 2/583* (2013.01); *A61F 2002/6827* (2013.01); *A61F 2002/6881* (2013.01); *A61F 2002/701* (2013.01); *A61F 2002/7625* (2013.01); *A61F 2002/7635* (2013.01); *A61F 2002/7665* (2013.01)

(58) Field of Classification Search
CPC ............... A61F 2/68; A61F 2/70; A61F 2/72; A61F 2002/701; A61F 2002/704
USPC ................... 623/24, 25, 57, 59, 60, 61, 62, 64
See application file for complete search history.

(56) References Cited

U.S. PATENT DOCUMENTS

| | | | |
|---|---|---|---|
| 4,685,928 | A | 8/1987 | Yaeger |
| 5,413,611 | A | 5/1995 | Haslam, II et al. |
| 5,447,403 | A | 9/1995 | Engler, Jr. |
| 6,379,393 | B1 | 4/2002 | Mavroidis et al. |
| 7,367,958 | B2 | 5/2008 | McBean et al. |
| 7,828,857 | B2 | 11/2010 | Farnsworth et al. |
| 7,835,823 | B2 | 11/2010 | Sillman et al. |
| 2009/0281637 | A1 * | 11/2009 | Martin ........................ 623/34 |
| 2010/0016990 | A1 | 1/2010 | Kurtz |
| 2010/0063601 | A1 | 3/2010 | Sankai |
| 2010/0268351 | A1 | 10/2010 | van der Merwe et al. |
| 2010/0274365 | A1 | 10/2010 | Evans et al. |

FOREIGN PATENT DOCUMENTS

| | | |
|---|---|---|
| WO | 2011/001136 A2 | 1/2011 |
| WO | 2011/036473 A1 | 3/2011 |

OTHER PUBLICATIONS

Simay, Motion Control Hand webpage: http://www.simaymedical.com/product-detail.aspx?id=25 ("Simay").*

(Continued)

*Primary Examiner* — Marcia Watkins
(74) *Attorney, Agent, or Firm* — Noah J. Hayward (57) ABSTRACT

A controller for a prosthetic device includes a processing section, an interface section connected to the processing section, and a power supply connected to both the processing section and the interface section. A dorsal indicator and a dorsal switch are disposed in a hand portion of the prosthetic device, and are both connected to the interface section.

18 Claims, 11 Drawing Sheets

(56) References Cited

OTHER PUBLICATIONS

Johannes et al., "An Overview of the Developmental Process for the Modular Prosthetic Limb", Johns Hopkins APL Technical Digest, vol. 30, No. 3 (2011) [availability date Mar. 7, 2011—prior art under 102(b)] ("Johannes").*

Brattbakken, "Embedded Control System for Cybernetic Wrist Prosthesis," Norwegian University of Science and Technology (NTNU), Master of Science in Engineering Cybernetics, Submission Jun. 2010.*

* cited by examiner

CONTROL SYSTEM FOR PROSTHETIC LIMB

STATEMENT OF GOVERNMENTAL INTEREST

This invention was made with government support under contract number N66001-06-C-8005 awarded by the Defense Advanced Research Projects Agency (DARPA) Defense Sciences Office (DSO). The government has certain rights in the invention.

BACKGROUND

The present disclosure relates generally to prosthetic devices. More particularly, the present disclosure relates to controllers and interfaces for modular prosthetic limbs.

There is an ongoing need for improved upper-extremity prostheses that restore full motor and sensory capability to upper extremity amputees. Modular prosthetic limb systems typically include motors, sensors, controllers, power supplies, mechanical and electrical connectors, interfaces, and feedback mechanisms, all of which are in addition to the prosthetic components themselves (limbs, hands, fingers, joints, etc.). Other hardware and software components are also often required. However, these prosthetic devices have very constrained space and power limitations, so that the devices remain lightweight and portable. Technologies capable of controlling such a large number of devices included in a conventional modular prosthetic limb are currently orders of magnitude larger than the limb itself, and consume substantial amounts of power. Accordingly, conventional control systems must currently be mounted external to the prosthetic components themselves, and therefore must be separately carried by the amputee, or mounted on a wheelchair, for example. Moreover, as prosthetic limbs become modular, such that individual components of the limbs can be "swapped out" as desired/needed, and as other advances are made in prosthetic technologies, there is an ongoing and increasing need for controllers and interfaces that provide flexible accommodations for multiple prosthetic components, while still minimizing the hardware and software footprints associated with the limbs and their associated controllers.

Accordingly, there is a significant need for improved modular prosthetic limb controllers and interfaces.

SUMMARY

Embodiments of the present invention include a controller for a prosthesis, such as an upper-extremity (e.g., arm) prosthesis, that is patient-controlled, is recognized via neural interfaces, is compact, e.g., is contained within a hand or palm portion of the prosthesis, and is perceived as natural with respect to function, weight, durability and comfort.

In accordance with one or more embodiments, a controller for a prosthetic device includes a processing section, an interface section connected to the processing section, and a power supply connected to the processing section and the interface section. A dorsal indicator is disposed in a hand portion of the prosthetic device and is connected to the interface section, and a dorsal switch is also disposed in the hand portion and connected to the interface section.

In accordance with another embodiment, a system for controlling a prosthetic device includes a limb controller, a power supply, a controller area network bus connected to the limb controller, and finger buses connected to the limb controller. The limb controller includes a processing section, an interface section connected to the processing section, an indicator disposed in a hand portion of the prosthetic device and connected to the interface section, and a dorsal switch disposed in the hand portion and connected to the interface section. The power supply is connected to the processing section and the interface section.

Other embodiments, including, but not limited to, apparatuses, systems and methods, for example, will be readily apparent from the detailed description and drawings presented herein.

BRIEF DESCRIPTION OF THE DRAWINGS

The above and other aspects, features and advantages of exemplary embodiments of the present invention will become even more readily apparent from the following detailed description, accompanied by the drawings, in which.

DETAILED DESCRIPTION

Exemplary embodiments of the present invention include a control system for a prosthesis, such as an upper-extremity (arm) prosthesis, for example. As can be determined from the embodiments described herein, the control system is compact, is patient-controlled, is recognized via neural interfaces, and is perceived by the patient as natural (with respect to function, weight, durability and comfort).

In general, example embodiments of a control system include an ultra-compact controller for a hand and limb, which communicates and controls numerous motors, sensors and devices in a modular prosthetic limb (MPL). In addition to being very small, e.g., capable of being located completely within the hand portion of the MPL, the controller is separated into both a processing section, as well as an interface section, which is physically separate from the processing section, to allow flexible interfaces without changing the associated control software. This architecture also provides for flexible power management of the MPL, considerably increasing battery life. The controller according to one or more embodiments includes five main interfaces, each described in further detail below but which, generally speaking, include: a controller area network, which provides a modular, reliable, and fault tolerant path for communications between the controller and the rest of the limb system, and which provides the controller intent from a neural system; RS-485 compatible custom finger buses, designed to have small hardware and software footprints, and which provide communication with all motor controllers and sensor nodes in the hand, allowing easy adaptability to more conventional devices, as desired; a power source from which the controller receives a single direct current (DC) power input from the limb and distributes this power to all electronics in the hand via microminiature connectors; a multi-color dorsal light emitting diode (LED) indicator, located in the hand, which the limb controller drives to provide patient feedback; and a dorsal pushbutton switch, also located in the hand, through which the controller interfaces with the controller area network bus to provide a variety of signals to the power system.

Conventional controllers that might be capable of controlling the volume and variety of interfaces and devices in the MPL described herein would be orders of magnitude larger, and consume considerably larger amounts of power, than in one or more embodiments of the present invention described herein. Although some conventional single board computers might have computational capabilities approaching those of the controller according to example embodiments of the present invention described herein, these single board computers are too large to fit within a prosthetic hand and, additionally, lack interfaces that could communicate with the number of external devices used in the MPL.

In contrast, example embodiments described herein are constructed by pairing a mobile processor with a low-power field programmable gate array (FPGA) over simple high speed serial interfaces. The use of the FPGA, together with the mobile processor, allows for combining numerous interfaces into a single package, and also allows for customization of the interface. Specifically, for example, using an FPGA allows the combination of multiple streams of communication traffic into a single serial link, thus enabling fast direct memory access (DMA) transfers from the processor to multiple destinations. In addition, the FPGA allows the inclusion of other, additional features in the limb controller, such as wakeup/sleep timers for the processor, for example. Accordingly, the FPGA provides a large amount of standard, custom, and semi-custom interfaces (as generally described above, and which are described in further detail below) while using a separate processor for the complex control algorithms that control the limb. This hybrid, segmented approach also allows for a clean division, providing a 2-board system, which naturally follows the curvature of the prosthetic hand, but also allows for alternative mounting options, at least one of which will be described below.

Figure 1:
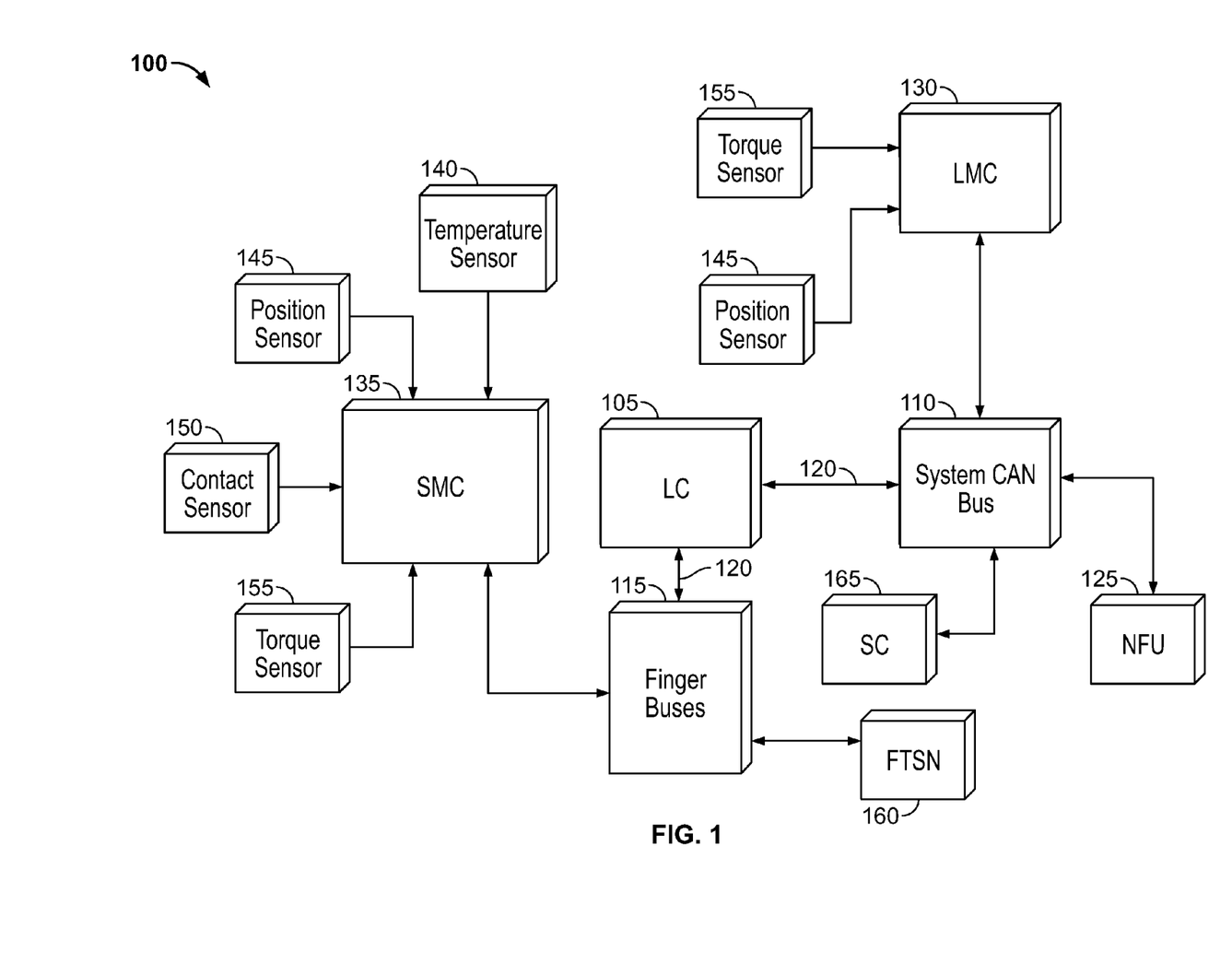
FIG. 1 is a block diagram of an exemplary embodiment of a system for controlling a prosthetic device.

Example embodiments of the present invention will now be described in greater detail with reference to the accompanying drawings. Referring to FIG. 1, which is a block diagram of a system 100 for controlling a prosthetic device, the system 100 includes a controller 105, e.g., a limb controller 105, a system controller area network (CAN) bus 110, and a plurality of finger buses 115 (only one shown in FIG. 1). The system CAN bus 110 and the finger buses 115 are connected to the limb controller 105 by input-output (I/O) interfaces 120. Relative to the system CAN bus 110, the finger buses 115 have small hardware and software footprints, since motor controllers and sensor nodes within the fingers have extremely restrictive space and power requirements.

The limb controller 105 is one component of an MPL (not shown). More particularly, the limb controller 105 is the central processor and manager of the MPL. Thus, the limb controller 105, which in one or more embodiments is packaged inside the hand of the MPL (and, more particularly, may be packaged completely within a palm portion of the hand), is responsible for high level coordinated control of the hand and large motor joints, as well as assorted system housekeeping activities and functions. However, it will be noted that, since the MPL system is a modular system, the limb controller 105 is also amenable to being mounted in other locations in or proximate to the MPL.

One function of the limb controller 105 is to control movement of the arm, hand and fingers of the MPL. Accordingly, user intent commands are received from a neural fusion unit (NFU) 125, which is connected to the limb controller 105 by the system CAN bus 110 and the I/O interface 120, as shown in FIG. 1. Commands from the NFU 125, as well as position statuses from a large motor controller (LMC) 130 and a plurality of small motor controllers (SMCs) 135 (only one shown in FIG. 1), which are received via the system CAN bus 110 and the finger buses 115, respectively, allow control algorithms in the limb controller 105 to generate new commands for the motor controllers 130 and 135.

In additional embodiments, the limb controller 105 uses the system CAN bus 110 for interfacing to additional devices/accessories, such as radio-frequency identification (RFID) readers, cellular/smart telephones and personal digital assistants (PDAs), for example, although additional or alternative embodiments are not limited thereto.

In one or more embodiments, the limb controller 105 is responsible for at least the following operations in the system 100: accepting user (e.g., patient or amputee) intent commands from the NFU 125; acquiring status information from the large motor controller 130 and providing user intent and status information to a limb control algorithm for processing; calculating new commands for the large motor controller 130 using the limb control algorithm; sending commands to the large motor controller 130 based on the output of the limb control algorithm; acquiring status information from the small motor controllers 135 in the hand; providing user intent and status information to a hand control algorithm for processing; calculating new commands for the small motor 135 using the hand control algorithm; sending commands to the small motor controllers 135 based on the output of the hand control algorithm; collecting sensor information and forwarding the data to a percept encoding algorithm; accepting configuration commands from a virtual integration environment (VIE)-NFU pass thru and forwarding the configuration commands to the appropriate limb node; accepting application programs from the VIE-NFU pass thru and forwarding the application programs to the appropriate limb node and/or storing the programs locally; accepting and processing mode change commands received from the VIE via the NFU; sending state commands to all of the nodes in the limb system; providing configuration parameter storage and distribution; and interfacing to a light emitting diode (LED) for visual user feedback.

The limb controller 105 also provides sensory data to the percept encoding algorithm from the sensors within the limb. This feedback allows the patient to sense external conditions without being limited to visual feedback.

As noted above, example embodiments include two types of motor controllers with which the limb controller 105 communicates. More specifically, the LMC 130 is used to move the upper arm, forearm and wrist of the MPL based on commands received from the limb controller 105. The LMC 130 also provides position feedback to the limb controller 105 for use by the abovementioned control algorithms. Communications between the LMC 130 and the limb controller 105 are accomplished by exchanging messages on the system CAN 110 bus. Similarly, the SMCs 135 are used to move the fingers and thumb of the MPL. In an example embodiment, the LMC 130 and the SMCs 135 communicate with the limb controller 105 using a serial interface, although alternative embodiments are not limited thereto.

The limb controller 105 also reports sensory information, such as position, temperature, torque and vibration, for example, to the patient (using the abovementioned percept encoding algorithm). Accordingly, temperature, position, contact and torque sensors 140, 145, 150 and 155, respectively, are located in the hand portion of the MPL. More specifically, as shown in FIG. 1, a given SMC 135 has connected to it a temperature sensor 140, a position sensor 145, a contact sensor 150 and a torque sensor 155. Although only one of the respective temperature, position, contact and torque sensors 140, 145, 150 and 155 are connected to the SMC 135 in FIG. 1, it will be noted that additional example embodiments are not limited thereto; rather, alternative embodiments may include more than one of each of the foregoing sensors connected to the SMC 135 (or to other components, for that matter). Specifically, for example, in a particular alternative embodiment, two (or more) position sensors 145 may be connected to the SMC 135. Additionally, the LMC 130 may have sensors connected to it, e.g., one or more of a position sensor 145 and/or a torque sensor 155, as is shown in FIG. 1.

In one or more embodiments, a serial interface is used to communicate sensor feedback to the limb controller 105, as well as to the NFU 125, via the system CAN bus 110. The limb controller 105 maintains the status of various data structures, which contain configuration parameters. These configuration parameters are maintained for real time tuning and observation. Accordingly, the user can monitor and modify the content of these values as desired. These data structures include, but are not limited, to limb positions, battery status, system state, and sensor information (e.g., temperature, torque, force and vibration.)

Management of system updates for nodes on the hand, as well as for the limb controller 105 itself, is performed by the limb controller 105. The limb controller 105 also maintains a record of transactions and system information for the limb. This includes a mechanism for storing information in memory, e.g., a flash memory, for later recall, as will be described in further detail below with reference to FIG. 2.

Still referring to FIG. 1, to ensure that the MPL uses the available power efficiently, the limb controller 105 monitors the battery charge state (such as by measuring the battery's voltage, for example) and sets an appropriate operating mode for the MPL based on the estimated available power remaining. If the available power is at a reduced level, for example, the limb controller 105 reduces the amount of current supplied to the motor controllers 130 and 135. To further conserve power, the limb controller 105 may enter a low power mode when a processor (shown in FIG. 2 and described below) is idle. The limb controller 105 subsequently comes out of the low power mode when an event that utilizes the processor occurs. In an example embodiment, a system CAN message or serial input from a sensor will cause the limb controller 105 to exit the low power mode.

The system CAN bus 110 is the MPL's system interface between the major nodes. In an example embodiment, the system CAN bus 110 is a multi-master interface that allows each device to send information to one or more of the other nodes on the system bus in a single- or multiple-message frame transmission. A priority messaging scheme is used by the system CAN bus 110 such that high priority messages are transmitted first. Based on this priority messaging capability, the system messages are defined to ensure that the messages are given sufficient priority to meet the system timing criteria.

As shown in FIG. 1, the system 100 according to an example embodiment further includes at least one fingertip sensor node (FTSN) 160 connected to the limb controller 105 via the finger bus(es) 115, as well as a socket controller (SC) 165 connected to the limb controller 105 via the system CAN bus 110.

The FTSN 160 has a number of sensors (not shown), including, but not being limited to, position sensors (e.g., potentiometer or Hall sensors), contact sensors (e.g., polyvinylidene difluoride contact sensors), fingertip sensors, and strain gauges, each of which provide various position, torque, and/or tactile feedback inputs to the limb controller 105. These sensors, distributed throughout the entire limb, provide the inputs for advanced control algorithms executed on the limb controller 105, as well as for sensory feedback to the patient.

The socket controller 165 is a module that sits directly at the attachment point of the MPL, and controls the direct physical connection point. This module is responsible for the attachment interface, as well as maintaining vacuum and a solid connection between the amputee/patient and the MPL.

Figure 2:
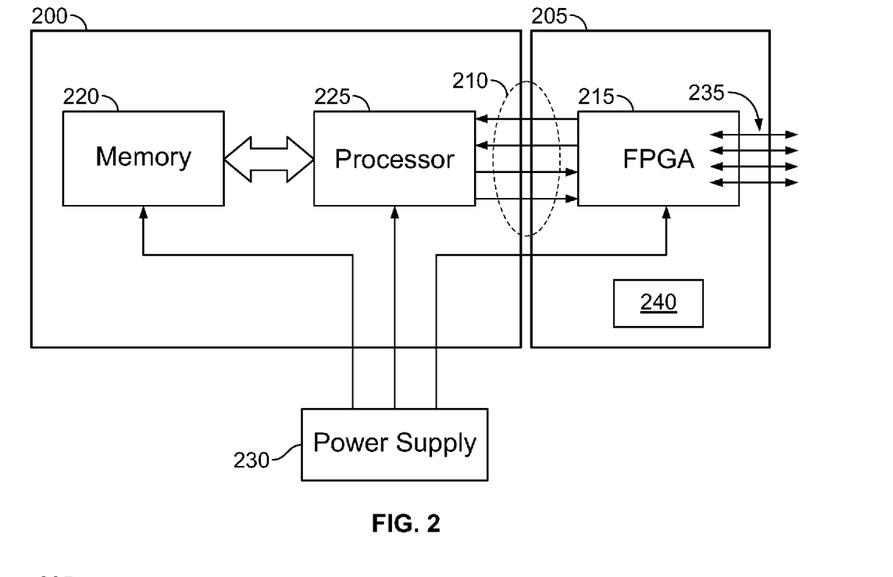
FIG. 2 is a block diagram of an exemplary embodiment of a limb controller.

Referring now to FIG. 2, which is a block diagram of an example embodiment of the limb controller 105, the limb controller 105 includes a processing section 200 and an interface section 205, connected to each other by a flex connect 210. In an example embodiment, the flex connect 210 includes multi-channel buffered serial ports (McBSPs), but alternative embodiments are not limited thereto. The interface section 205 is connected to the system CAN bus 110 and the finger buses 115 by corresponding I/O interfaces 120 (FIG. 1).

Figure 4A:
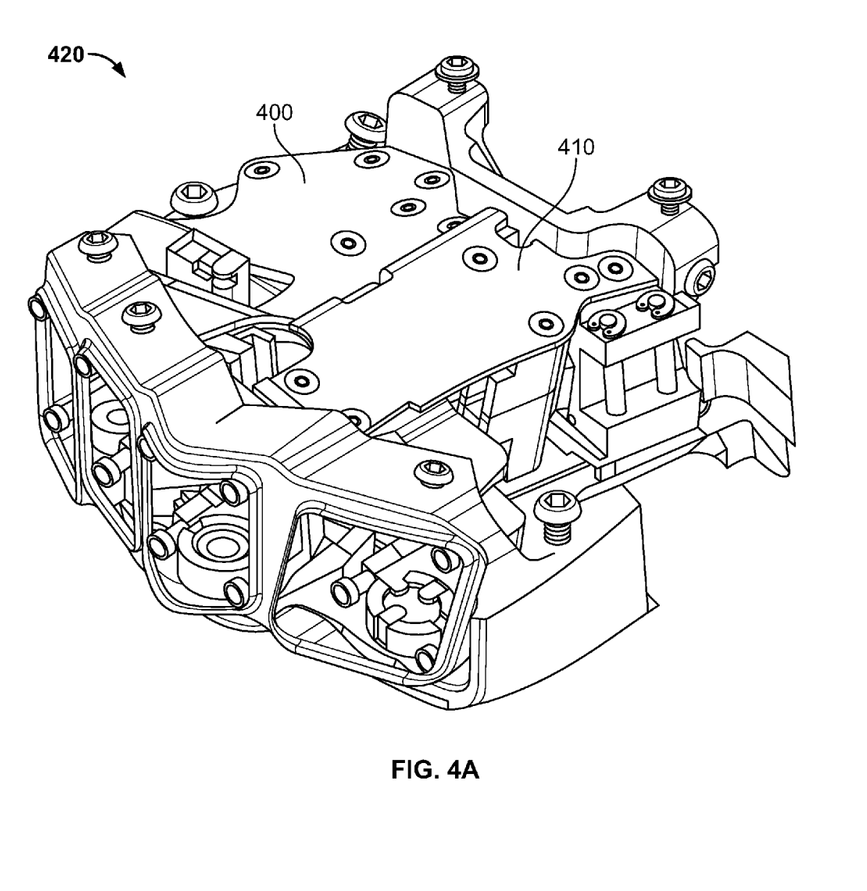
FIGS. 4A-4C are perspective dorsal views of an exemplary embodiment of a hand portion of a prosthetic limb.

The interface section 205 includes a an FPGA 215 which, in a one embodiment, is an Actel IGLOO® AGL250 FPGA, although it will be understood that additional example embodiments are not limited thereto. A board on which the FPGA 215 is disposed is connected to a standard single-pole momentary, normally open switch, which is located in a palm portion of the hand of the MPL, as will be described in further detail below with reference to FIGS. 4-6.

The FPGA 215 provides a connection between a processor 225 and the MPL. More particularly, the FPGA acts as a universal asynchronous receiver/transmitter (UART) interface, in which the FPGA 215 takes a high speed, e.g., about 13 megabits per second (Mbps) or greater, serial stream from the processor 225, parallelizes the high speed serial stream, and dispatches messages to the appropriate destination in the MPL. Further to its UART role, the FPGA 215 buffers transmit messages so that the processor 225 can use an extremely efficient mechanism or protocol (e.g., direct memory access and/or high speed buffered serial) to burst all message traffic in a short or compressed period of time, if desired. The FPGA 215 also receives messages from one or more of the aforementioned interfaces, encodes them with the appropriate source information, and sends them over the flex connect 210 (which includes McBSPs, for example) to the processor 225. In one embodiment, this data is not buffered by the FPGA (or is minimally buffered), since buffers (not shown) in the processor 225 may buffer these messages without CPU intervention.

Figure 6:
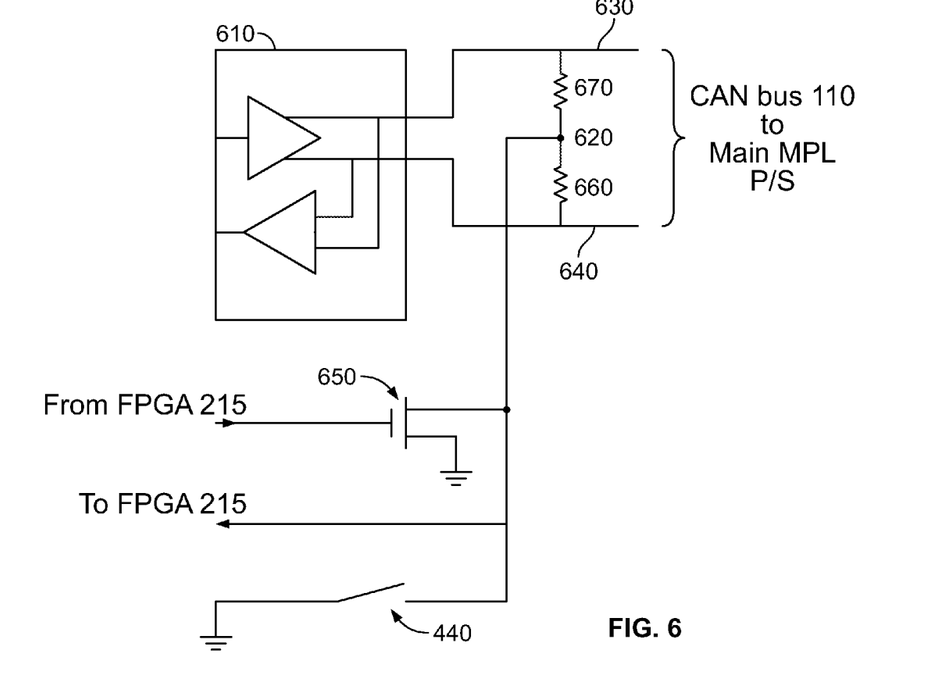
FIG. 6 is a schematic diagram of an exemplary embodiment of a dorsal switch circuit.

The FPGA 215 also supports system CAN bus 110 transmission, where the FPGA 215 takes a high speed serial stream, containing a CAN message, from the processor 225 and sends the message over the main limb CAN bus (FIG. 6). More specifically, the FPGA 215 provides two software modalities: interrupt-driven message transmission on a message-by-message basis; and buffered transmission of multiple messages without intervention from the processor 225.

In addition, the FPGA 215 also supports CAN bus reception, e.g., taking CAN messages from the main limb system bus, serializing and sending the messages to the processor 225 for processing, while providing hardware filtering to discard messages that the limb controller 105 does not need (to reduce interrupt burden on the processor 225), while still interrupting the processor 225 for specially-tagged CAN messages, thus allowing the processor 225 to ignore certain messages for a time while still being made aware of other, relatively urgent messages.

Still referring to FIG. 2, the processing section 200 also includes a memory 220, as well as the aforementioned processor 225 that runs limb control and supervisory functions, connected to the memory 220. In an example embodiment, the memory 220 includes one or more "NAND" flash and/or synchronous dynamic random-access (SDRAM) memories in a common package, such as a die-stacked package, and the processor/CPU 225 is a Texas Instruments OMAP® 3503 processor, although alternative example embodiments are not limited to the foregoing components. In an example embodiment, the memory 220 is implemented in a package-on-package (POP) configuration, which is to say that, in the memory 220, two or more packages are installed on top of each other, e.g., are vertically stacked.

A power supply 230 supplies power to the abovementioned components of the processing section 200 and the interface section 205. In an example embodiment, the power supply 230 provides DC power and is located separate from the limb controller 105 in a wrist portion of the MPL. Alternatively, the power supply 230 may be integral to, i.e. may be a part of, the limb controller 105 located completely in the palm portion of the MPL. More specifically, in an alternative example embodiment, the power supply 230 may be physically disposed in the processing section 200, although additional embodiments are not limited to the components or arrangements thereof described above.

Still referring to FIG. 2, the interface section 205 includes I/O interfaces 235, which include, but are not limited to, the controller area network bus 110 and finger bus(es) 115 shown in FIG. 1 and was described in greater detail above. A dorsal switch 240 is disposed in the interface section 205, as will be described in further detail below with reference to FIGS. 4-6.

Figure 3A:
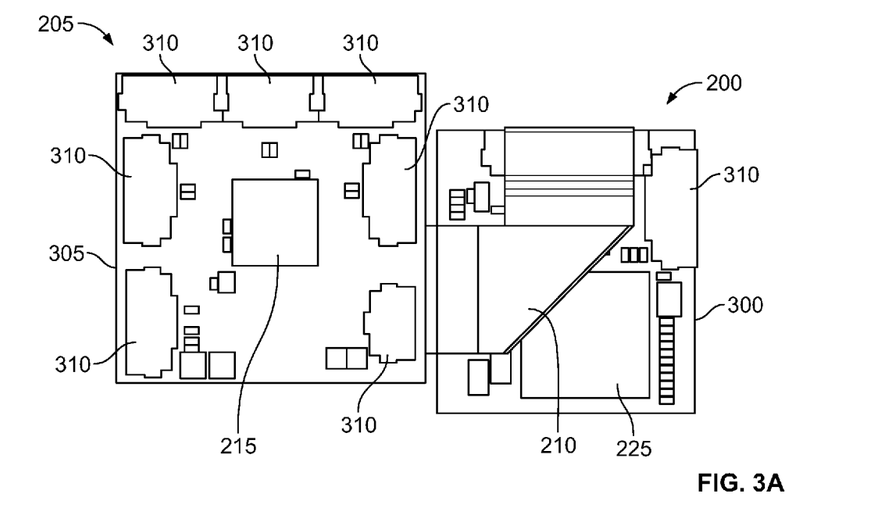
FIGS. 3A-3C are perspective views of the limb controller shown in FIG. 2.
Figure 3B:
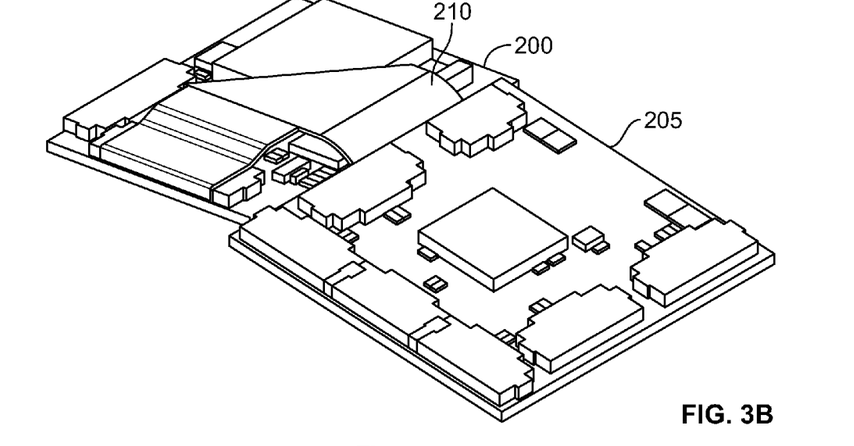
Figures 3C, 3D:
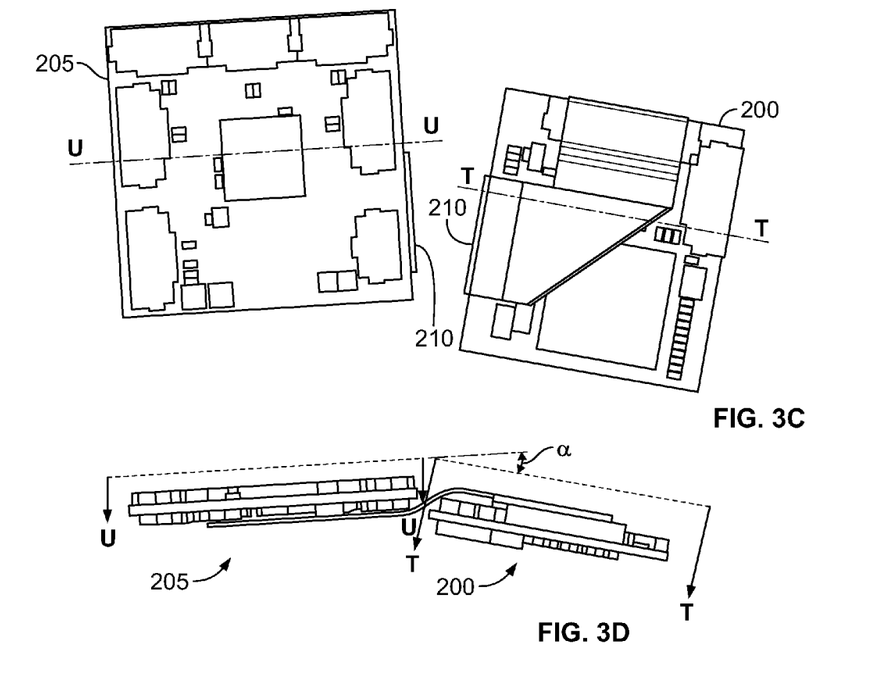
FIG. 3D illustrates partial cross-sectional views taken lines U-U and T-T of FIG. 3C.
Figure 4B:
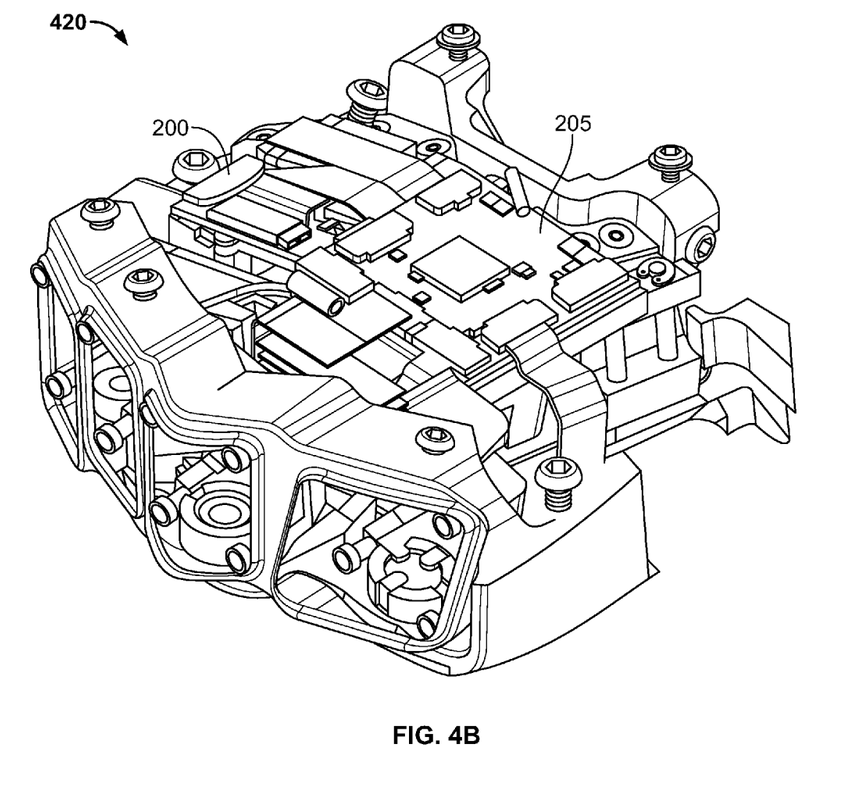
Figure 4C:
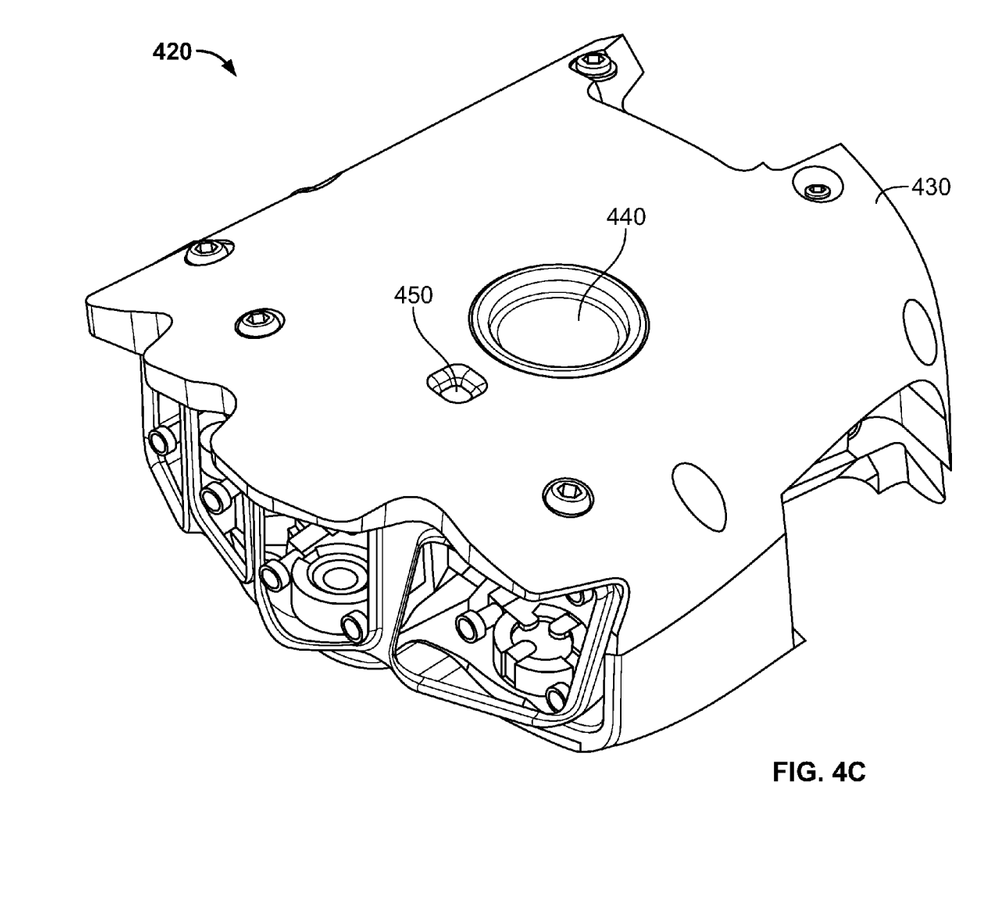

FIGS. 3A-3C are perspective views of the limb controller 105 shown in FIG. 2, FIG. 3D includes partial cross-sectional views taken lines U-U and T-T of FIG. 3C, and FIGS. 4A-4C are perspective dorsal views of an example embodiment of a hand portion of a prosthetic limb according to one or more example embodiments of the present invention. As will now be described in further detail with reference to FIGS. 3 and 4, the limb controller 105 hardware is disposed separately on a processor section rigid board 300 (hereinafter "CPU board 300") for the processing section 200, and an interface section rigid board 305 (hereinafter "FPGA board 305") for the interface section 205. The CPU board 300 and the FPGA board 305 are connected by the flex connect 210 via McBSP connectors, for example, on each of the rigid boards 300 and 305. The CPU board 300 and the FPGA board 305 are respectively disposed on a CPU shelf 400 and an FPGA shelf 410 (FIG. 4A) in a hand portion 420 of the MPL. More particularly, the CPU board 300 and the FPGA board 305 are disposed on their respective shelves 400 and 410 (FIG. 4B) and are covered by a dorsal shell 430 over a central portion, e.g., a palm portion, of the hand portion 420. As will be described in greater detail below with reference to FIGS. 5-6, a dorsal switch 440 and a dorsal indicator 450 are disposed in the dorsal shell 430 (FIG. 4C).

As shown in FIG. 3, the CPU board 300 and the FPGA board 305 are physically separate from each other, and are offset, e.g., are not located directly above each other, in the hand portion, but are electrically connected to each other by the flex connect 210. In an example embodiment, planes defined by the boards 300 and 305 are angled with respect to each other by an angle α (FIG. 3D), such that the boards 300 and 305 conform to the contour of the dorsal shell 430 (FIG. 4C), e.g., to conform to the shape of the hand in the MPL and, more particularly, to the shape of the MPL palm. The angle α may be from about (e.g., approximately) 10 degrees to about 20 degrees and, in one example embodiment, the angle α is about 15 degrees, although alternative embodiments are not limited to the foregoing angles. Moreover, additional embodiments are not limited to the foregoing general arrangement of the boards 300 and 305 at all; rather, as will be described in further detail below with references to FIGS. 7 and 8, the boards 300 and 305 may be stacked directly on top of each other in the hand portion 420 of the MPL.

As can be seen in FIGS. 3 and 4, the FPGA board 305 is disposed above (as viewed in FIG. 4B), but is offset from, the CPU board 300. Further, the boards 300 and 305 both include jacks 310, e.g., mating receptacles 310, for connecting the boards 300 and 305 to other components of the MPL. Although not specifically labeled in FIG. 3, non-limiting examples of the mating receptacles 310, include a thumb mechanical hardware (MHW) section, abduction and adduction (AbAd) MHW sections, finger (e.g., index, middle, ring, and little finger) MHW sections, a wrist MHW section, a debug section and the dorsal switch 440.

Using the two separate boards 300 and 305 in the palm portion of the MPL in the manner described above makes efficient use of available space in the hand portion 420. Specifically, this arrangement provides extra area on the boards, and allows for connection of multiple interfaces. Implementing the memory 220 in a POP configuration, as described above, further saves space in the hand portion 420.

Using two separate boards also allows both of the boards 300 and 305 to be completely rigid, which provides a significantly wider range of options related to fabricating the boards 300 and 305. Further, the CPU board 300 and the FPGA board 305 can be connected with a minimum of signals, and a logical separation between the processing section 200 and the interface section 205 of the limb controller 105 allows for easier debugging, as well as reduced operational risk, in that any problems the CPU board 300 will not affect the FPGA board 305 (and vice versa).

Figure 5:
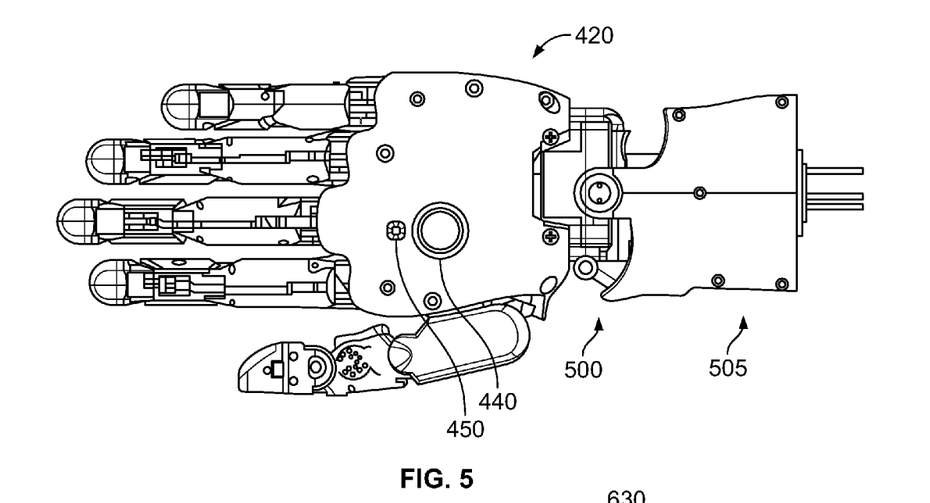
FIG. 5 is a perspective dorsal view of an exemplary embodiment of a hand portion of a prosthetic limb.

FIG. 5 is a perspective dorsal view of a hand portion of the MPL, which includes the hand portion 420 (with the aforementioned palm portion included therein), as well as a wrist portion 500 and an arm portion 505 (not fully shown in FIG. 5). FIG. 6 is a schematic diagram of an example embodiment of a circuit for the dorsal switch 440. Construction and operation of the dorsal switch 440 and the dorsal indicator 450 will now be described in greater detail with reference to FIGS. 5 and 6.

As shown in FIG. 5, the dorsal switch 440 and dorsal indicator 450 are disposed in the palm portion of the MPL. The FPGA board 305 (FIG. 3) connects, through two pins, for example, to the dorsal indicator 450, which in an example embodiment is a dual-LED device. The FPGA 215 sources or sinks current to the two pins, lighting either a red or green-yellow LED, for example. Additionally, by lighting one LED, or rapidly cycling between the two LEDs, the dorsal indicator 450 can display red, green, orange or other color indicators to provide information/feedback to the user of the MPL.

During normal MPL operations, e.g., when the MPL is powered on and not in receipt of a power up or power down command from the FPGA 215, a CAN interface chip 610 electrically connects the FPGA 215 to the system CAN bus 110. For power-down and power-up operations, however, the FPGA 215 is also connected to the dorsal switch 440 via an associated mating receptacle 310 (FIG. 3). In an example embodiment, the dorsal switch 440 is a single-pole, normally open, momentary switch, but alternative example embodiments are not limited thereto. Thus, the contact in the dorsal switch 440 will normally be pulled up by a resistor (not shown) on the FPGA board 305, and will be shorted to ground when the dorsal switch 440 is pressed. The dorsal switch 440 is also connected to a center tap of a split terminator for the system CAN bus 110, which allows button presses to be seen locally by both the FPGA 215 and the processor 225 in the limb controller 105, and additionally allows button presses to be seen outside the limb controller 105, such as by the power supply 230 (in embodiments when it is external to the limb controller 105), so that the power supply 230 uses the switch signal to control power to the MPL. Additionally, the FPGA 215 provides the status of the dorsal switch 440 to the processor 225. Furthermore, the FPGA 215 determines if a switch press indicates impending power-down, in which case the FPGA 215 interrupts the processor 225.

Thus, the user is able to turn the MPL on and off with a simple press of the dorsal switch 440. In addition, the limb controller 105 is able to command power off in response to system errors or other criteria. In an example embodiment, when the MPL is turned off, it is in an exceptionally low power state, e.g., the processor 225 is completely powered off, i.e. does not require or use any power. Moreover, the MPL does not require any additional wires between the limb controller 105 in the hand portion 420 (FIG. 4) and the power system (which may in some embodiments be located as far away from the hand portion as the forearm of the MPL). This allows for only having four wires cross the wrist joint (via a slip ring, for example).

To implement the above and other advantages, the limb controller 105 according to one or more example embodiments sends power-on and power-off signals to the power supply 230 via lines of the system CAN bus 110 that cross the wrist (in an example embodiment, the CAN bus lines are the only electrical lines that cross the wrist). This is accomplished simply, without a complex signaling protocol, since the processor 225 is not running (i.e. is completely without power) during the power-off state of the MPL. Specifically, in an example embodiment, a CAN common node 620 (FIG. 6) voltage at the power supply 230 is monitored. Power-on and power-off commands are piggybacked on top of the normal communications lines, and the system CAN bus 110 uses a differential standard, where high and low levels are determined by a relative difference between two lines, e.g., between a CAN high line 630 (FIG. 6) and a CAN low line 640, which connect to a main limb power system ("P/S") (not shown), which is different from the power supply 230 and is disposed in the MPL outside of the hand portion 420, e.g., above the wrist portion 500 of the MPL. This provides noise immunity, and further provides for back channel signaling, in which the power-on and power-off commands appear as noise to the communications bus chips, while the power supply 230 is still able to interpret the signal and use it to control power to the MPL.

As shown in FIG. 6, the limb controller 105 (FIG. 2) controls power to the MPL by sending a power down command, via the FPGA 215, to drive the gate of a transistor 650 (FIG. 6) to a high level to connect the CAN common node 620 voltage, measured between a first resistor 660 and a second resistor 670 to ground. Alternatively, the user can command power-down by mechanically connecting the CAN common node 620 to ground by pressing the dorsal switch 440.

Similarly, the user commands power-up by pressing the dorsal switch 440, and the power-up is actuated using a small bias voltage on the CAN common node lines, without requiring any power or signals from the processor 225, thereby allowing the processor 225 to be completely powered down when the MPL is turned off, which considerably reduces power consumption of the MPL, while still allowing the user full and simple control of power to the MPL.

Figure 7A:
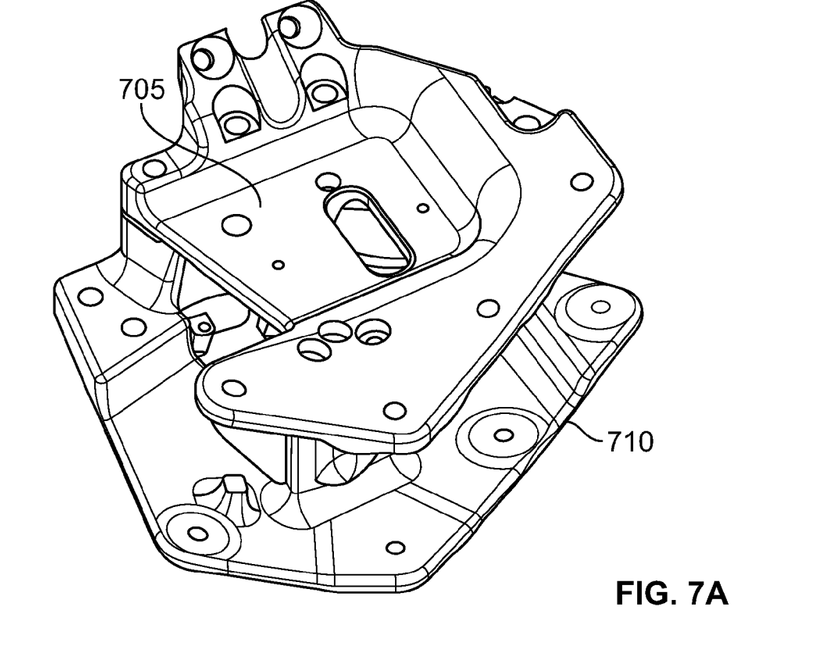
FIGS. 7A-7C are cut-away palm views of an exemplary embodiment of a hand portion of a prosthetic limb.
Figure 7B:
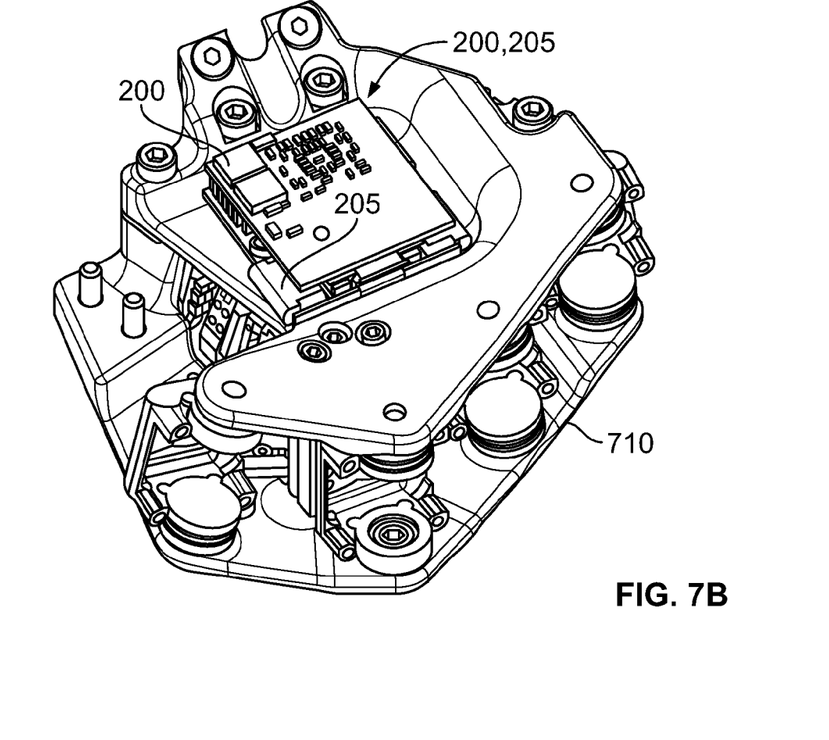
Figure 7C:
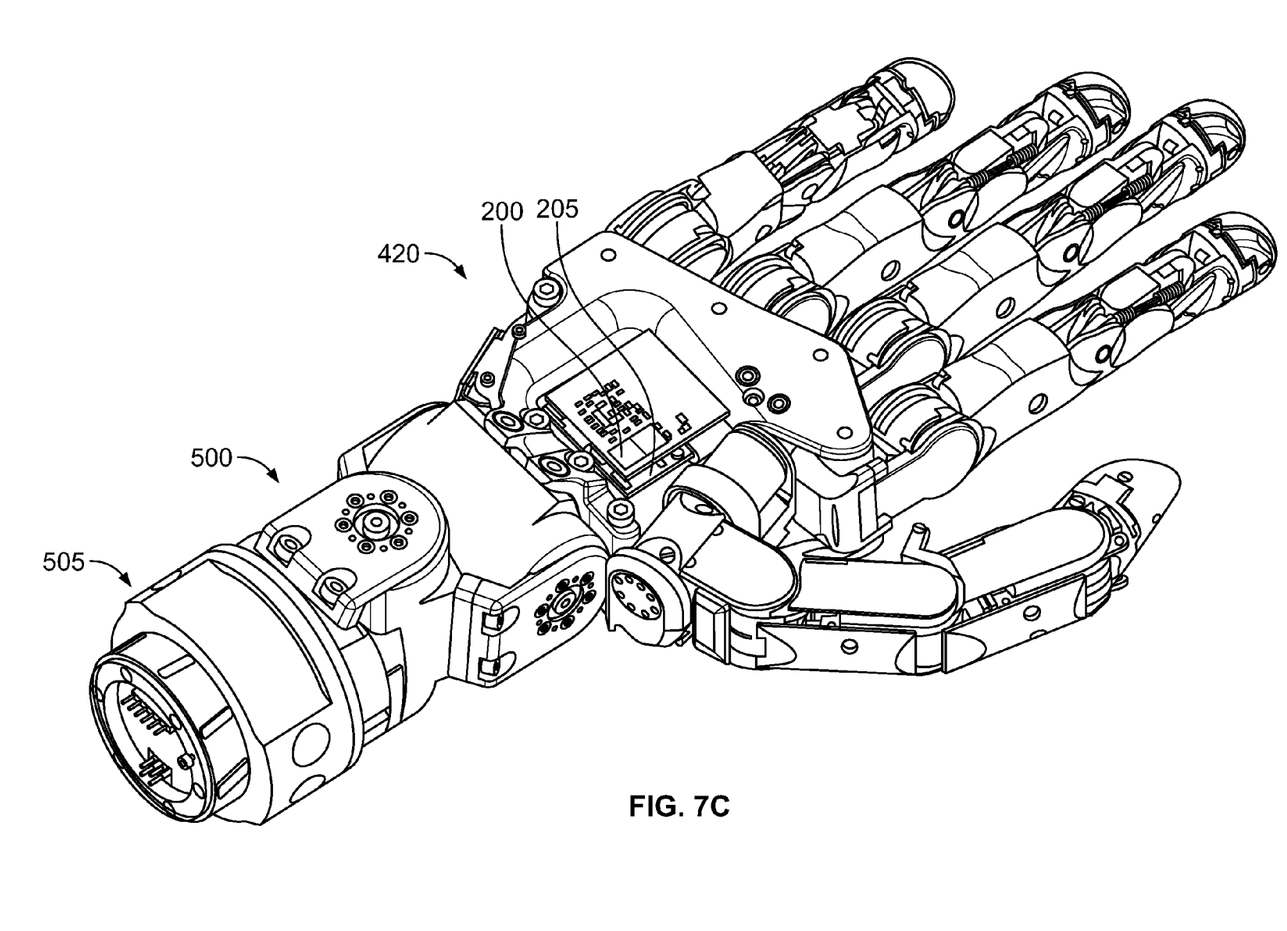
Figure 8A:
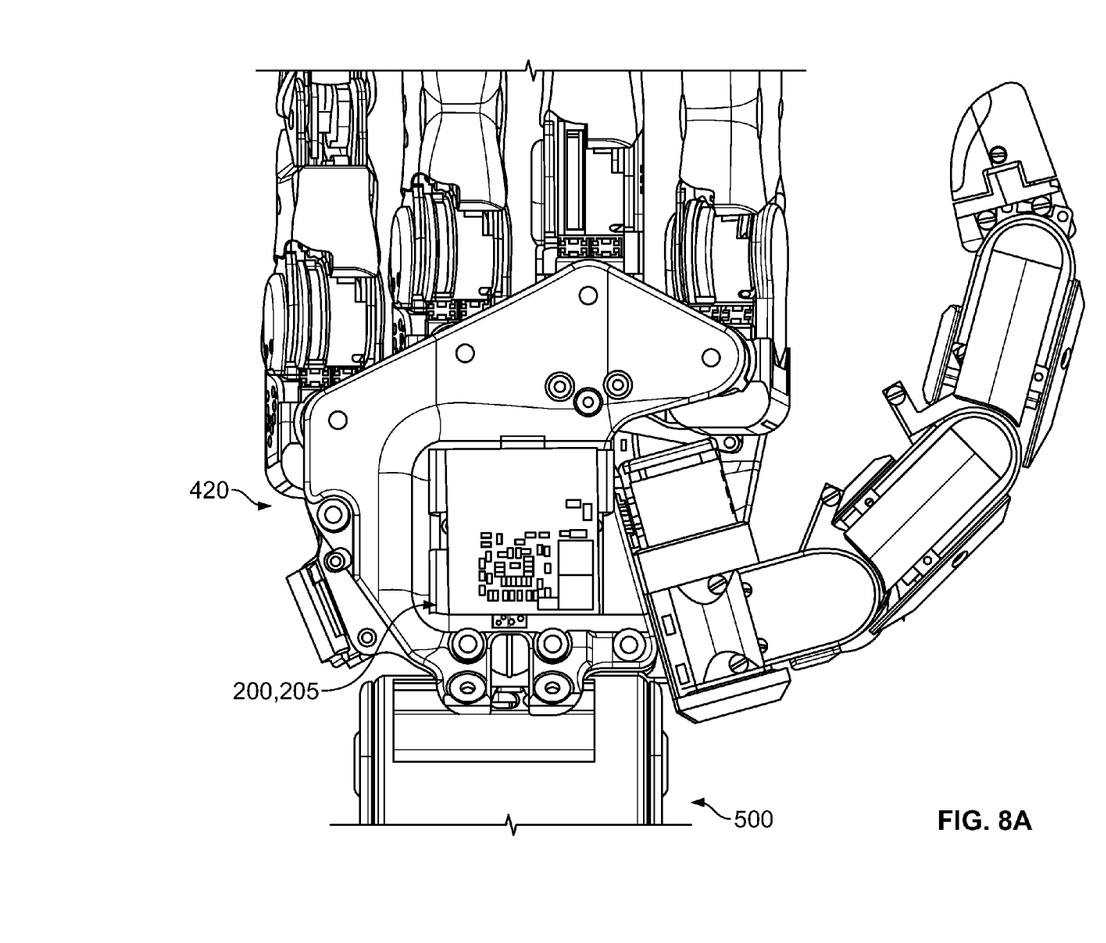
FIGS. 8A-8B are cut-away palm views of an alternative exemplary embodiment of a hand portion of a prosthetic limb.

Referring now to FIGS. 7 and 8, which are cut-away palm views of a hand portion 420 of an MPL according to an alternative example embodiment, the processing section 200 (having disposed thereon the CPU board 300) and the interface section 205 (having disposed thereon the FPGA board 305), described above with reference to FIGS. 3-5, are stacked (disposed) directly on top of one another (i.e. are not offset from each other) in the hand portion 420 of the MPL. Specifically, as shown in FIG. 7B, processing and interface sections 200 and 205 are both disposed in a single tray 705 of a hand portion endoskeleton 710 of the hand portion 420 of the MPL. More specifically, the processing section 200 is disposed above the interface section 205 (as viewed in FIGS. 7B and 7C), although alternative embodiments are not limited thereto.

Figure 8B:
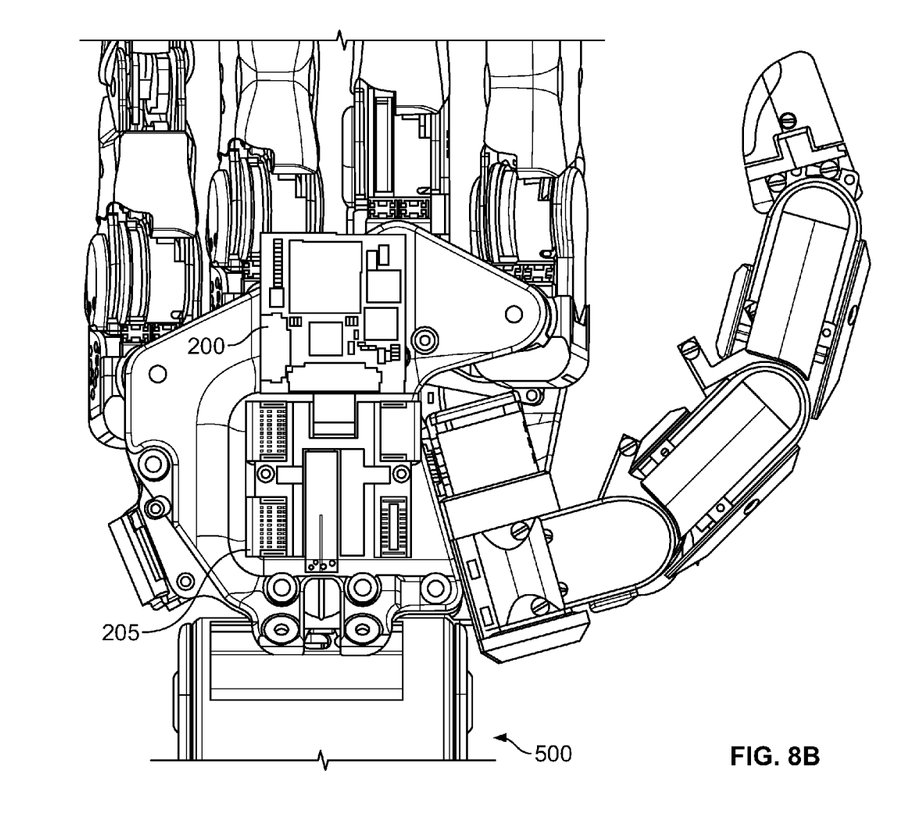

In addition, in an example embodiment, the processing section 200 is mounted in the tray 705 of the hand portion 420 such that the processing section 200 can be folded, e.g., pivoted, away from the interface section 205 to expose the interface section 205 without the need to physically remove or unplug the processing section 200, as shown in FIG. 8B. This considerably improves the ease of performing testing, repairs, or maintenance on both the processing section 200 and the interface section 205, and further improves the lifetime and reliability of the limb controller 105, since there is no need to repeatedly disconnect and reconnect components (physically and/or electrically) to perform testing, repairs, or maintenance.

Having herein described various embodiments of improved modular prosthetic limb controllers and interfaces, it will be understood that additional modifications can be made thereto. Therefore, the above description shall not be construed as limiting the scope of the invention. Rather, those of ordinary skill in the art will readily envision additional modifications within the spirit and scope of the present invention as defined by the appended claims.

What is claimed is:

1. A controller for a prosthetic device, comprising:
a processing section;
an interface section connected to the processing section;
a power supply connected to the processing section and the interface section;
a dorsal indicator disposed in a hand portion of the prosthetic device and connected to the interface section; and
a dorsal switch disposed in the hand portion and connected to the interface section, wherein
the controller is completely disposed in a hand portion of the prosthetic device,
the processing section and the interface section are disposed on a processing board and an interface board, respectively,
the processing board and the interface board are disposed directly on top of each other in a tray of the hand portion, and
one of the processing section and the interface section is configured to pivot to expose the other of the processing section and the interface section without disconnecting the processing section from the interface section and without disconnecting the processing section or the interface section from the hand portion.

2. The controller of claim 1, further comprising a flex connect which connects the processing section to the interface section, wherein the processing section comprises:
a processor; and
a memory connected to the processor.

3. The controller of claim 2, wherein the processor does not use any power when the prosthetic device is turned off.

4. The controller of claim 2, wherein
the memory is implemented in a package-on-package configuration, and
interface section comprises a field programmable gate array.

5. The controller of claim 1, wherein
the interface section comprises a plurality of mating receptacles, and
said plurality of mating receptacles comprises:
an interface debug mating receptacle; and
one or more mating receptacles for a thumb, an index finger, a middle finger, a ring finger and a little finger.

6. The controller of claim 1, wherein the interface section comprises:
a controller area network bus;
finger buses; and
input-output interfaces which connect the controller area network bus and the finger buses to one or more components of a plurality of components.

7. The controller of claim 6, wherein the plurality of components comprises a small motor controller, a large motor controller, a neural fusion unit, a socket controller, a fingertip sensor node, a temperature sensor, a position sensor, a contact sensor and a torque sensor.

8. The controller of claim 1, wherein
the prosthetic device is a modular prosthetic limb.

9. The controller of claim 8, wherein
the processing section and the interface section are disposed on a processing board and an interface board, respectively,
the processing board and the interface board are offset from each other and angled with respect to each other to conform to a contour of a dorsal shell of the hand portion, and
an angle formed by planes defined by the processing board and the interface board is from about 10 degrees through about 20 degrees.

10. A system for controlling a prosthetic device, comprising:
a limb controller comprising:
a processing section;
an interface section connected to the processing section;
an indicator disposed in a hand portion of the prosthetic device and connected to the interface section; and
a dorsal switch disposed in the hand portion and connected to the interface section;
a power supply connected to the processing section and the interface section;
a controller area network bus connected to the limb controller; and
finger buses connected to the limb controller.

11. The system of claim 10, further comprising:
a large motor controller connected to the system controller area network bus;
a neural fusion unit connected to the system controller area network bus; and
a socket controller connected to the system controller area network bus.

12. The system of claim 10, wherein
the processing section comprises:
a processor; and
a memory connected to the processor, and
the memory is implemented in a package-on-package configuration.

13. The system of claim 12, wherein
the prosthetic device is a modular prosthetic limb, and
the limb controller is completely disposed in the hand portion of the modular prosthetic limb.

14. The system of claim 13, wherein
the processing section and the interface section are disposed on a processing board and an interface board, respectively,
the processing board and the interface board are offset from each other and angled with respect to each other to conform to a contour of a dorsal shell of the hand portion, and
an angle formed by planes defined by the processing board and the interface board is from about 10 degrees through about 20 degrees.

15. The system of claim 14, wherein the angle formed by the planes is equal to about 15 degrees.

16. The system of claim 13, wherein
the processing section and the interface section are disposed on a processing board and an interface board, respectively, and
the processing board and the interface board are disposed directly on top of each other in a tray of the hand portion of the modular prosthetic limb.

17. The system of claim 16, wherein one of the processing section and the interface section is configured to pivot to expose the other of the processing section and the interface section without disconnecting the processing section from the interface section and without disconnecting the processing section or the interface section from the hand portion.

18. The system of claim 10, wherein
the processing section does not use any power when the prosthetic device is turned off, and
the limb controller is configured to power up the prosthetic device based on a bias voltage of the controller area network bus.

* * * * *